(12) United States Patent
Seymour

(10) Patent No.: US 6,340,120 B1
(45) Date of Patent: Jan. 22, 2002

(54) SCENT DISPENSING DEVICE

(76) Inventor: David K. Seymour, 609 Country Club Dr., Newark, OH (US) 43055

( * ) Notice: Subject to any disclaimer, the term of this patent is extended or adjusted under 35 U.S.C. 154(b) by 0 days.

(21) Appl. No.: 09/484,463

(22) Filed: Jan. 14, 2000

(51) Int. Cl.$^7$ ................................................. A61L 9/04
(52) U.S. Cl. .............................. 239/59; 239/57; 239/55; 239/34
(58) Field of Search ............................. 239/59, 58, 57, 239/55, 53, 34

(56) References Cited

U.S. PATENT DOCUMENTS

| | | | | |
|---|---|---|---|---|
| 2,086,631 A | * | 7/1937 | Munro | |
| 2,755,954 A | * | 7/1956 | Antritter | |
| 3,945,568 A | * | 3/1976 | Bychowski | |
| 3,976,246 A | * | 8/1976 | Hauri et al. | |
| 4,937,431 A | * | 6/1990 | Jameson et al. | |
| 5,465,521 A | * | 11/1995 | Baker et al. | |
| 5,549,247 A | * | 8/1996 | Rossman et al. | |

* cited by examiner

Primary Examiner—David A. Scherbel
Assistant Examiner—Christopher S. Kim

(57) ABSTRACT

A scent dispensing device for dispensing a scent while protecting the scented material from the elements. The scent dispensing device includes a container comprising a base portion and a cover portion for covering the base portion. The cover portion has a peripheral wall integrally coupled to a top wall. The peripheral wall has a peripheral edge. A first hanging structure for hanging the container is fixedly coupled to an exterior surface of the top wall. The base portion has a peripheral wall and a bottom wall. The peripheral wall has a lip thereon. The lip has a size and a shape adapted to fit in the cover such that the lip may be releasably coupled in the cover. A plurality of slots releases the scent. The slots extend through the peripheral wall of the bottom portion.

13 Claims, 2 Drawing Sheets

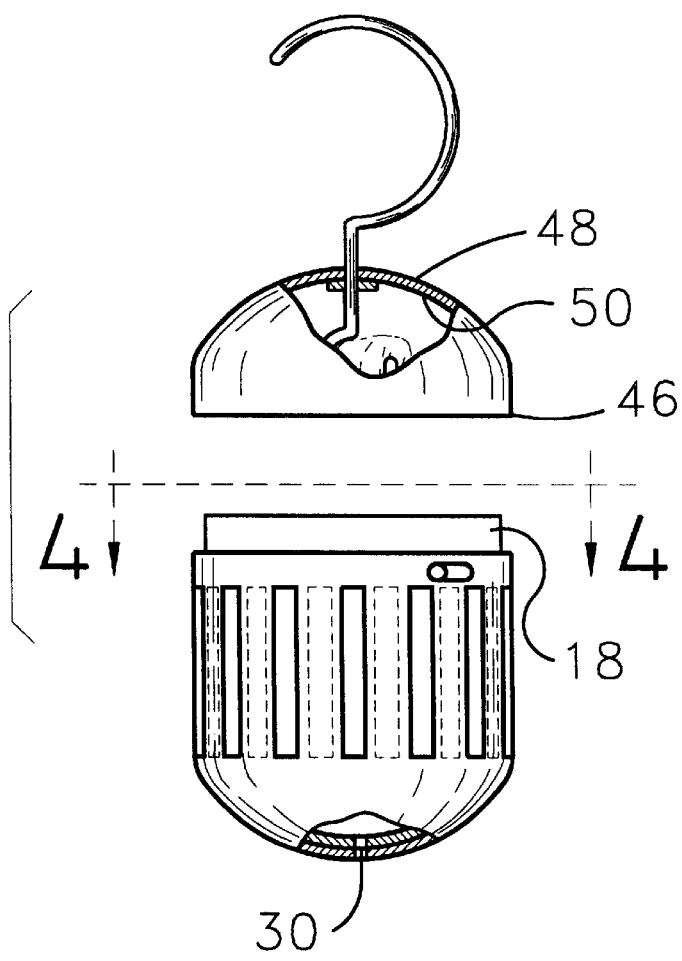
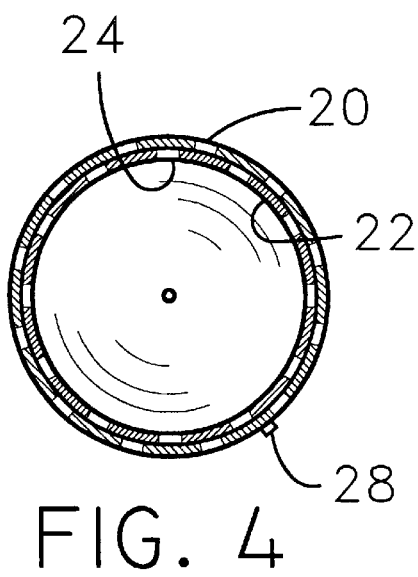
FIG. 3
FIG. 4

SCENT DISPENSING DEVICE

BACKGROUND OF THE INVENTION

1. Field of the Invention

The present invention relates to scent dispensers and more particularly pertains to a new scent dispensing device for dispensing a scent while protecting the scented material from the elements.

2. Description of the Prior Art

The use of scent dispensers is known in the prior art. More specifically, scent dispensers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,746,019; U.S. Pat. No. 5,595,137; U.S. Pat. No. 4,441,372; U.S. Pat. No. 2,111,025; U.S. Pat. No. 5,555,663; and U.S. Des. Pat. No. 324,730.

While these devices fulfill their respective, particular objectives and requirements, the aforementioned patents do not disclose a new scent dispensing device. The inventive device includes a container comprising a base portion and a cover portion for covering the base portion. The cover portion has a peripheral wall integrally coupled to a top wall. The peripheral wall has a peripheral edge. A first hanging means for hanging the container is fixedly coupled to an exterior surface of the top wall. The base portion has a peripheral wall and a bottom wall. The peripheral wall has a lip thereon. The lip has a size and a shape adapted to fit in the cover such that the lip may be releasably coupled in the cover. A plurality of slots releases the scent. The slots extend through the peripheral wall of the bottom portion.

In these respects, the scent dispensing device according to the present invention substantially departs from the conventional concepts and designs of the prior art, and in so doing provides an apparatus primarily developed for the purpose of dispensing a scent while protecting the scented material from the elements.

SUMMARY OF THE INVENTION

In view of the foregoing disadvantages inherent in the known types of scent dispensers now present in the prior art, the present invention provides a new scent dispensing device construction wherein the same can be utilized for dispensing a scent while protecting the scented material from the elements.

The general purpose of the present invention, which will be described subsequently in greater detail, is to provide a new scent dispensing device apparatus and method which has many of the advantages of the scent dispensers mentioned heretofore and many novel features that result in a new scent dispensing device which is not anticipated, rendered obvious, suggested, or even implied by any of the prior art scent dispensers, either alone or in any combination thereof.

To attain this, the present invention generally comprises a container comprising a base portion and a cover portion for covering the base portion. The cover portion has a peripheral wall integrally coupled to a top wall. The peripheral wall has a peripheral edge. A first hanging means for hanging the container is fixedly coupled to an exterior surface of the top wall. The base portion has a peripheral wall and a bottom wall. The peripheral wall has a lip thereon. The lip has a size and a shape adapted to fit in the cover such that the lip may be releasably coupled in the cover. A plurality of slots releases the scent. The slots extend through the peripheral wall of the bottom portion.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new scent dispensing device apparatus and method which has many of the advantages of the scent dispensers mentioned heretofore and many novel features that result in a new scent dispensing device which is not anticipated, rendered obvious, suggested, or even implied by any of the prior art scent dispensers, either alone or in any combination thereof.

It is another object of the present invention to provide a new scent dispensing device which may be easily and efficiently manufactured and marketed.

It is a further object of the present invention to provide a new scent dispensing device which is of a durable and reliable construction.

An even further object of the present invention is to provide a new scent dispensing device which is susceptible of a low cost of manufacture with regard to both materials and labor, and which accordingly is then susceptible of low prices of sale to the consuming public, thereby making such scent dispensing device economically available to the buying public.

Still yet another object of the present invention is to provide a new scent dispensing device which provides in the apparatuses and methods of the prior art some of the advantages thereof, while simultaneously overcoming some of the disadvantages normally associated therewith.

Still another object of the present invention is to provide a new scent dispensing device for dispensing a scent while protecting the scented material from the elements.

Yet another object of the present invention is to provide a new scent dispensing device which includes a container comprising a base portion and a cover portion for covering the base portion. The cover portion has a peripheral wall integrally coupled to a top wall. The peripheral wall has a peripheral edge. A first hanging means for hanging the container is fixedly coupled to an exterior surface of the top wall. The base portion has a peripheral wall and a bottom wall. The peripheral wall has a lip thereon. The lip has a size and a shape adapted to fit in the cover such that the lip may be releasably coupled in the cover. A plurality of slots releases the scent. The slots extend through the peripheral wall of the bottom portion.

Still yet another object of the present invention is to provide a new scent dispensing device that may be closed to prevent the scent from dissipating when not needed.

Even still another object of the present invention is to provide a new scent dispensing device that may be economically filled with any scent a hunter may need.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic front view of the present invention.

FIG. 4 is a schematic plan view of the present invention.

DESCRIPTION OF THE PREFERRED EMBODIMENT

Figure 1:
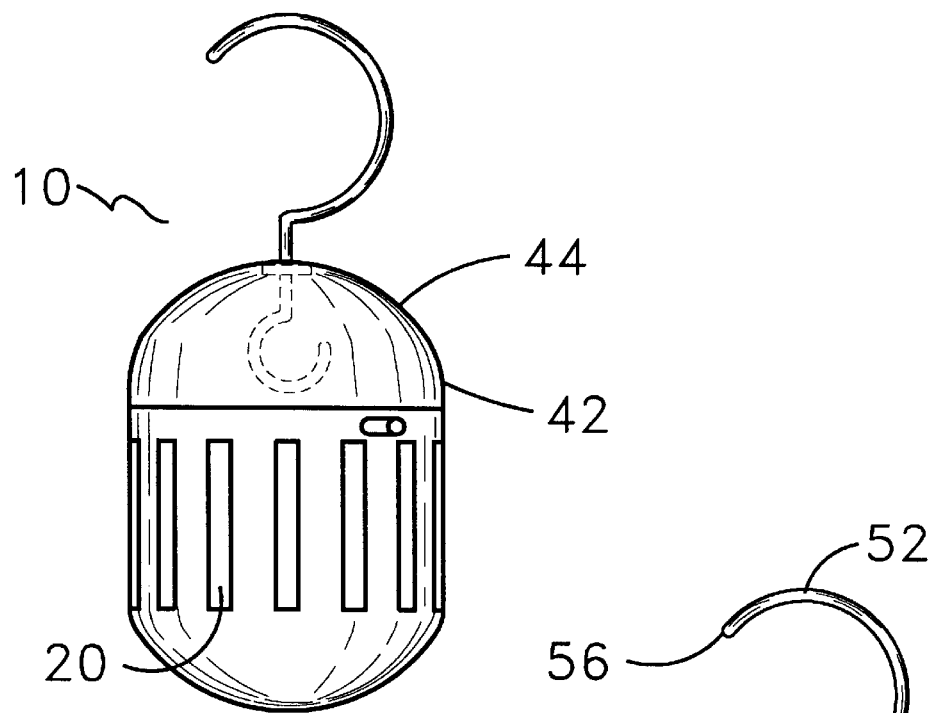
FIG. 1 is a schematic front view of a new scent dispensing device according to the present invention.
Figure 2:
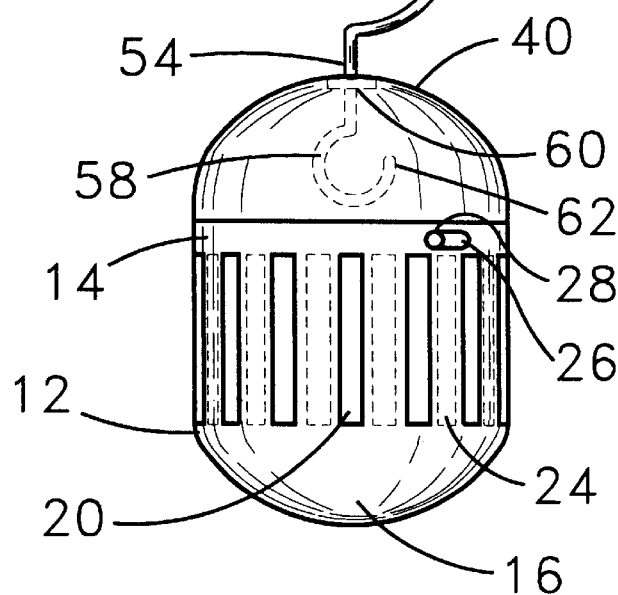
FIG. 2 is a schematic front view with the slots of the bottom portion open.

With reference now to the drawings, and in particular to FIG. 1 through 4 thereof, a new scent dispensing device embodying the principles and concepts of the present invention and generally designated by the reference numeral 10 will be described.

As best illustrated in FIGS. 1 through 4, the scent dispensing device 10 generally comprises a base portion 12 and a cover portion 40.

The cover portion 40 covers the base portion 12. The cover portion 40 has a peripheral wall 42 integrally coupled to a top wall 44. The peripheral wall 42 has a peripheral edge 46. The peripheral wall 42 has a generally cylindrical shape. The top wall 44 has a domed shape such that a rounded portion of the top wall 44 extends away from the peripheral wall 42. The cover portion 40 has an interior area bounded by the peripheral wall. The cover portion has an exterior surface 48 and an interior surface 50.

A first hanging means for hanging the container comprises a first hook 52 having a first end 54 and a second end 56. The first end of the first hook 54 is fixedly coupled to the exterior surface 48 of the top wall 44. The first end 54 of the first hook is generally located in a central portion of the top wall 44.

A second hanging means hangs a scented material in the interior area of the cover. If there is no second hanging means, the scented material may be placed in the bottom portion of the container. The second hanging means is a second hook 58 having a first end 60 and a second end 62. The first end 60 of the second hook 58 is fixedly coupled to an interior surface 50 of the top wall 44. The first end 60 of the second hook 58 is generally located in a central portion of the top wall 44. The first end 60 of the second hook 58 is integrally coupled to the first end 54 of the first hook 52.

The base portion 12 has a peripheral wall 14 and a bottom wall 16. The peripheral wall 14 of the base portion has a generally cylindrical shape. The peripheral wall 14 of the base portion has an inner diameter substantially equal to an inner diameter of the peripheral wall 42 of the cover portion 40. The peripheral wall 14 of the base portion has an annular lip 18 extending therefrom. The annular lip 18 is on an inner surface of the peripheral wall 14 of the base portion. The annular lip 18 extends upwardly away from the bottom wall 16. The annular lip 18 has an outside diameter generally equal to the inner diameter of the peripheral wall 42 of the cover 40 such that the annular lip 18 may be releasably coupled in the cover portion 40. The bottom wall 16 is preferably domed.

A plurality of slots 20 releases the scent. The slots 20 extend through the peripheral wall 14 of the bottom portion 12. Each of the slots 20 is elongate. Each of the slots 20 is orientated generally parallel to each other. Each of the slots 20 is orientated generally parallel to a longitudinal axis of the peripheral wall 14 of the base portion 12.

An inner peripheral wall 22 selectively opens and closes the slots 20. The inner peripheral wall 22 is rotatably mounted in the bottom portion 12. The inner peripheral 22 wall has dimensions adapted to abut the inner peripheral wall against the inner surface of the peripheral wall 14 of the bottom portion 12. The inner peripheral wall 22 has slots 24 therethrough. Each of the slots 24 in the inner peripheral wall 22 is located to coincide with one of the slots 20 in the peripheral wall 14 of the base portion 12.

An aperture 26 is in the peripheral wall 14 of the base portion 12. The aperture 26 is located generally adjacent to the annular lip 18.

An actuating means that selectively rotates the inner peripheral wall 22 with respect to the bottom portion 12 is a protruding member 28 fixedly coupled to the inner peripheral wall 22. The protruding member 28 is located such that the protruding member extends through the aperture 26.

A bore 30 drains the collection of any condensation in the bottom portion 12 of the container. The bore 30 is in a central portion of the bottom wall 16 of the bottom portion 12.

In use, scent is placed on material such as a cotton ball and hung from the second hook 58. When a user wishes for the scent to be released, the protruding member 28 is moved to open the slots 20. The cover portion 40 protects the scented material from the elements and allows the scent to last longer. The container is then hung from a branch, nail or other such appendage in an area desired by the user.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A scent dispensing device, said device comprising:
    a container, said container comprising:
        a base portion;
        a cover portion for covering said base portion, said cover portion having a peripheral wall integrally coupled to a top wall, said peripheral wall having a peripheral edge;
        a first hanging means for hanging said container, said first hanging means being fixedly coupled to an exterior surface of said top wall;
        said base portion having a peripheral wall and a bottom wall, said peripheral wall having a lip thereon, said lip having a size and a shape adapted to fit in said cover such that said lip may be releasably coupled in said cover;
        a plurality of slots for releasing said scent, said slots extending through said peripheral wall of said bottom portion;
        an inner peripheral wall positioned in said base portion and having dimensions adapted to abut said inner peripheral wall against an inner surface of said peripheral wall of said base portion, said inner peripheral wall having slots therethrough, each of said slots in said inner peripheral wall being located to coincide with one of said slots in said peripheral wall of said base portion, said inner peripheral wall being rotatably mounted in said bottom portion for selectively opening and closing said slots.
        a first hook having a first end and a second end, said first end of said first hook being fixedly coupled to said top wall such that said second end extends away from said top wall; and
        a second hook having a first end and a second end, said first end of said second hook being fixedly coupled to said first end of said first hook, said second end of said second hook extending into an interior of said container for hanging a scented material in the interior of said container.

2. The scent dispensing device as in claim 1, wherein said cover portion further comprises:
    said peripheral wall of said cover having a peripheral edge, said peripheral wall having a generally cylindrical shape, said top wall having a domed shape such that a rounded portion of said top wall extends away from said peripheral wall.

3. The scent dispensing device as in claim 1, wherein said base portion further comprises:
    said peripheral wall of said base portion having a generally cylindrical shape, said peripheral wall of said base portion having an inner diameter being substantially equal to an inner diameter of said peripheral wall of said cover portion, said lip being an annular lip.

4. The scent dispensing device as in claim 1, wherein the bottom wall of said base portion is domed.

5. The scent dispensing device as in claim 1, wherein said plurality of slot comprises:
    each of said slots being elongate, each of said slots being orientated generally parallel to each other, each of said slots being orientated generally parallel to a longitudinal axis of said peripheral wall of said base portion.

6. The scent dispensing device as in claim 1, further comprising:
    an aperture in said peripheral wall of said base portion, said aperture being located generally adjacent to said annular lip; and
    an actuating means for selectively rotating said inner peripheral wall with respect to said bottom portion, said actuating means being a protruding member, said protruding member being fixedly coupled to said inner peripheral wall, said protruding member being located such that said protruding member extends through said aperture.

7. The scent dispensing device as in claim 1, further comprising:
    a bore for drainage of condensation, said bore being in said bottom wall of said bottom portion, said bore being in a central portion of said bottom wall.

8. A scent dispensing device, said device comprising:
    a container, said container comprising:
        a base portion;
        a cover portion for covering said base portion, said cover portion having a peripheral wall integrally coupled to a top wall, said peripheral wall having a peripheral edge, said peripheral wall having a generally cylindrical shape, said top wall having a domed shape such that a rounded portion of said top wall extends away from said peripheral wall, said cover portion having an interior area bounded by said peripheral wall, said cover portion having an exterior surface and an interior surface;
        a first hanging means for hanging said container, said first hanging means comprising a first hook having a first end and a second end, said first end of said first hook being fixedly coupled to said exterior surface of said top wall, said first end of said first hook being generally located in a central portion of said top wall;
        a second hanging means for hanging a scented material in said interior area of said cover, said second hanging means being a second hook having a first end and a second end, said first end of said second hook being fixedly coupled to an interior surface of said top wall, said first end of said second hook being generally located in a central portion of said top wall, said first end of said second hook being integrally coupled to said first end of said first hook;
        said base portion having a peripheral wall and a bottom wall, said peripheral wall of said base portion having a generally cylindrical shape, said peripheral wall of said base portion having an inner diameter being substantially equal to an inner diameter of said peripheral wall of said cover portion, said peripheral wall of said base portion having an annular lip extending therefrom, said annular lip being on an inner surface of said peripheral wall of said base portion, said annular lip extending upwardly away from said bottom wall, said annular lip having an outside diameter generally equal to said inner diameter of said peripheral wall of said cover such that said annular lip may be releasably coupled in said cover, said bottom wall being domed;

a plurality of slots for releasing said scent, said slots extending through said peripheral wall of said bottom portion, each of said slots being elongate, each of said slots being orientated generally parallel to each other, each of said slots being orientated generally parallel to a longitudinal axis of said peripheral wall of said base portion; an inner peripheral wall for selectively opening and closing said slots, said inner peripheral wall being rotatably mounted in said bottom portion, said inner peripheral wall having dimensions adapted to abut said inner peripheral wall against said inner surface of said peripheral wall of said bottom portion, said inner peripheral wall having slots therethrough, each of said slots in said inner peripheral wall being located to coincide with one of said slots in said peripheral wall of said base portion;

an aperture in said peripheral wall of said base portion, said aperture being located generally adjacent to said annular lip;

an actuating means for selectively rotating said inner peripheral wall with respect to said bottom portion, said actuating means being a protruding member, said protruding member being fixedly coupled to said inner peripheral wall, said protruding member being located such that said protruding member extends through said aperture; and a bore for drainage of condensation, said bore being in said bottom wall of said bottom portion, said bore being in a central portion of said bottom wall.

9. A scent dispensing device, said device comprising:

a container, said container comprising:

a base portion;

a cover portion for covering said base portion, said cover portion having a peripheral wall integrally coupled to a top wall, said peripheral wall having a peripheral edge;

a first hanging means for hanging said container, said first hanging means being fixedly coupled to an exterior surface of said top wall;

said base portion having a peripheral wall and a bottom wall, said peripheral wall having a lip thereon, said lip having a size and a shape adapted to fit in said cover such that said lip may be releasably coupled in said cover;

a plurality of slots for releasing said scent, said slots extending through said peripheral wall of said bottom portion;

wherein said cover portion further comprises said peripheral wall of said cover having a peripheral edge, said peripheral wall having a generally cylindrical shape, said top wall having a domed shape such that a rounded portion of said top wall extends away from said peripheral wall;

wherein said first hanging means further comprises said first hanging means comprising a first hook having a first end and a second end, said first end of said first hook being fixedly coupled to said exterior surface of said top wall, said first end of said first hook being generally located in a central portion of said top wall;

wherein said base portion further comprises said peripheral wall of said base portion having a generally cylindrical shape, said peripheral wall of said base portion having an inner diameter being substantially equal to an inner diameter of said peripheral wall of said cover portion, said lip being an annular lip;

wherein said base portion comprises said bottom wall being domed;

wherein said plurality of slot comprises each of said slots being elongate, each of said slots being orientated generally parallel to each other, each of said slots being orientated generally parallel to a longitudinal axis of said peripheral wall of said base portion; and an inner peripheral wall for selectively opening and closing said slots, said inner peripheral wall being rotatably mounted in said bottom portion, said inner peripheral wall having dimensions adapted to abut said inner peripheral wall against said inner surface of said peripheral wall of said bottom portion, said inner peripheral wall having slots therethrough, each of said slots in said inner peripheral wall being located to coincide with one of said slots in said peripheral wall of said base portion.

10. The scent dispensing device as in claim 9, further comprising:

an aperture in said peripheral wall of said base portion, said aperture being located generally adjacent to said annular lip; and an actuating means for selectively rotating said inner peripheral wall with respect to said bottom portion, said actuating means being a protruding member, said protruding member being fixedly coupled to said inner peripheral wall, said protruding member being located such that said protruding member extends through said aperture.

11. The scent dispensing device as in claim 10, further comprising:

a bore for drainage of condensation, said bore being in said bottom wall of said bottom portion, said bore being in a central portion of said bottom wall.

12. The scent dispensing device as in claim 9, further comprising:

a second hanging means for hanging a scented material in an interior area of said cover.

13. The scent dispensing device as in claim 9, wherein said second hanging means comprises:

said second hanging means being a second hook having a first end and a second end, said first end of said second hook being fixedly coupled to an interior surface of said top wall, said first end of said second hook being generally located in a central portion of said top wall.

* * * * *